United States Patent
Fatiny et al.

(10) Patent No.: US 10,327,865 B2
(45) Date of Patent: Jun. 25, 2019

(54) COMPOSITE RESTORATION ROLLER

(71) Applicant: King Abdulaziz University, Jeddah (SA)

(72) Inventors: Fahad Ibrahim Fatiny, Jeddah (SA); Turki Y. Alhazzazi, Jeddah (SA); Helal M. Sonbul, Jeddah (SA)

(73) Assignee: King Abdulaziz University, Jeddah (SA)

( * ) Notice: Subject to any disclaimer, the term of this patent is extended or adjusted under 35 U.S.C. 154(b) by 0 days.

(21) Appl. No.: 15/823,894

(22) Filed: Nov. 28, 2017

(65) Prior Publication Data

US 2019/0159866 A1    May 30, 2019

(51) Int. Cl.
*A61C 3/08*    (2006.01)

(52) U.S. Cl.
CPC ...................... *A61C 3/08* (2013.01)

(58) Field of Classification Search
CPC .. A61C 3/00; A61C 3/06; A61C 3/005; A61C 1/12; A45D 34/041
USPC ................. 433/141, 156, 164, 163
See application file for complete search history.

(56) References Cited

U.S. PATENT DOCUMENTS

| | | | |
|---|---|---|---|
| 150,943 A | 5/1874 | Dennett | |
| 882,711 A * | 3/1908 | Pearsall et al. | A61C 3/08 433/164 |
| 1,676,715 A | 7/1928 | Snyder | |
| 3,921,044 A | 11/1975 | McShirley | |
| 4,396,375 A * | 8/1983 | Gores | A61C 9/0033 433/141 |
| 4,552,531 A | 11/1985 | Martin | |
| 4,586,901 A | 5/1986 | Tanaka et al. | |
| 4,636,171 A | 1/1987 | Martin | |
| 4,767,325 A | 8/1988 | Kopunek et al. | |
| 4,892,481 A | 1/1990 | Kopunek et al. | |
| 4,904,185 A | 2/1990 | McSpadden | |
| 4,940,350 A | 7/1990 | Kim | |
| 5,030,093 A | 7/1991 | Mitnick | |
| 5,040,981 A | 8/1991 | Oliva | |
| 5,098,292 A | 3/1992 | Lazarof | |
| 5,176,754 A | 1/1993 | Hirzel | |
| 5,242,302 A | 9/1993 | Riehm | |
| 6,024,564 A * | 2/2000 | Kesling | A61C 19/043 433/141 |
| 6,071,122 A | 6/2000 | Kilcher et al. | |

(Continued)

FOREIGN PATENT DOCUMENTS

| | | | |
|---|---|---|---|
| EP | 1 741 404 A1 | 1/2007 | |
| GB | 218345 A * | 7/1924 | A61H 13/00 |
| JP | 2010-240279 A | 10/2010 | |

OTHER PUBLICATIONS

"CompoRoller—Composite Modeling Instrument", Kerr Dental, https://www.kerrdental.com/kerr-restoratives/comporoller-composite-modeling-instrument#docs, Apr. 24, 2016, 3 pages.

*Primary Examiner* — Wade Miles
*Assistant Examiner* — Matthew P Saunders
(74) *Attorney, Agent, or Firm* — Oblon, McClelland, Maier & Neustadt, L.L.P.

(57) ABSTRACT

A dental instrument with an interchangeable frustum roller with a fixed apical tip for unobstructed viewing a working surface on a tooth and for rapidly, precisely and homogenously distributing a restorative material on the surface of a tooth while avoiding adherence of an applied restorative material to the dental instrument.

19 Claims, 6 Drawing Sheets

(56) References Cited

U.S. PATENT DOCUMENTS

| | | | |
|---|---|---|---|
| 6,186,786 B1 | 2/2001 | Trushkowsky | |
| 6,206,698 B1 | 3/2001 | Billingsley | |
| 6,280,187 B1 | 8/2001 | Slone | |
| 6,409,505 B1 * | 6/2002 | Kesling | A61C 19/043 433/141 |
| 6,511,320 B2 * | 1/2003 | Esposito | A61C 3/00 433/141 |
| 6,991,459 B2 | 1/2006 | Lashmore | |
| 6,997,709 B2 | 2/2006 | Kangasniemi et al. | |
| 8,376,744 B2 * | 2/2013 | Latiolais | A61C 3/00 433/141 |
| 8,602,779 B2 | 12/2013 | Simons | |
| 8,616,880 B2 | 12/2013 | Viscomi | |
| 2003/0211443 A1 | 11/2003 | Magee | |
| 2004/0229186 A1 | 11/2004 | Slone | |
| 2005/0130099 A1 * | 6/2005 | Besek | A61C 3/08 433/80 |
| 2005/0255428 A1 | 11/2005 | Coopersmith | |
| 2006/0003288 A1 | 1/2006 | Lashmore | |
| 2008/0014553 A1 | 1/2008 | Garrison et al. | |
| 2008/0213731 A1 | 9/2008 | Fishburne | |
| 2011/0143303 A1 | 6/2011 | Kilcher et al. | |
| 2012/0301848 A1 | 11/2012 | O'Donnell | |
| 2016/0228221 A1 * | 8/2016 | Cho | A61C 3/00 |

* cited by examiner

COMPOSITE RESTORATION ROLLER

BACKGROUND

Field of the Disclosure

This invention relates to a dental instrument for homogeneously applying, packing, or shaping tooth restorative material, and specifically, to a dental instrument with an interchangeable roller tip comprising a fixed apical tip and a frustum (truncated conical) roller for distributing the restorative material while avoiding incorporating bubbles into a dental restoration.

Description of the Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention.

Standard filling and restoration materials in dentistry include composite materials that often contain binders in the form of hardened organic substances and fillers. Generally, dental restorative materials that are polymerizable with light must be applied within a short time frame because during their careful application and subsequent contouring they can start to polymerize due to ambient light. Similarly, the application and contouring of dental restoratives that incorporate a chemical catalyst must also be completed before substantial polymerization of the restorative.

A disadvantage of these composite materials is their tendency to adhere more or less to the instrument that is used to apply or shape them. As a result, the composite material has a tendency to be drawn off from the edges of the cavity, to inhomogeneously distribute on the tooth surface, and to form air bubbles during the distribution.

While the clinical performance of dental composites has been significantly improved over the past decade through modifications in formulation that include using more stable polymerization promoters for greater color stability; incorporating high concentrations of finely ground fillers to produce adequate strength and excellent wear resistance while retaining translucency; adding radio pacifying agents for improved diagnostics; and utilizing dentin adhesives, there are still significant problems which limit the use of composites, especially in posterior teeth.

Many composite materials remain very technique-sensitive, due to the extensive contraction which accompanies polymerization and which negatively influences marginal sealing. In addition, composite materials are generally considered to have inadequate mechanical properties and wear resistance in contact areas to serve as total replacements for amalgams.

Current efforts have focused on development of non- or minimally-shrinking dental composites containing spiro-orthocarbonates as additives to dimethacrylates or epoxy-base resins, and the production of alternative filler materials for ideal wear resistance and aesthetics.

The instruments for distributing a restorative dental material typically comprise a steel instrument with an uncoated working tip portion or a tip portion coated with a metal alloy such as nickel-titanium. They may also be composed of a plastic material with or without working tip that is treated or coated with a non-stick material. For example, a dental instrument may be coated with Teflon® to reduce adhesion of a restorative composite. However, even with such coatings, a restorative material may adhere or otherwise be difficult to apply.

Alternatively, it has been proposed to reduce composite adherence to a dental instrument by providing a discontinuous surface that includes an array of micro-pits, see U.S. Pat. No. 6,071,122. While that instrument achieves reduced adhesion of the composite material, homogeneous distribution free of air bubbles has not been fully achieved and strength, durability and aesthetic properties of a restoration are detrimentally affected. Other potential approaches include the use of dental instruments with roller tips. For example, Besek, et al., U.S. 20050130099, describe a dental instrument with a monolithic roller tip which is mounted on an internal axial rotating member so that the monolithic tip can rotate around a longitudinal axis. However, this configuration can make the uniform application of a material difficult and may introduce air bubbles into the applied restorative material. These problems may be caused by rotation of the apex of the rotating tip which can produce sheer forces that result in mixing of a composite material and air or saliva, especially in or around narrow or confined dental surfaces.

Consequently, there is a need for a dental instrument that is effective for homogeneously distributing a composite restorative material to a tooth surface, that avoids the integration of air bubbles into a restoration, and thus provides superior strength, durability, color and aesthetics.

SUMMARY OF THE INVENTION

The present invention provides a dental instrument with a working tip having a rotating conical body and a fixed, non-rotating tip that can distribute a restorative material on or into a tooth surface, quickly, precisely, and homogeneously with little adherence of the restorative material to the working tip while eliminating or reducing the incorporation of air bubbles into the restorative material. The fixed tip does not generate mixing or sheering forces that a rotating apical tip would while the frustum roller substantially reduces adherence of dental composite materials to the instrument.

BRIEF DESCRIPTION OF THE DRAWINGS

A more complete appreciation of the disclosure and many of the attendant advantages thereof will be readily understood by reference to the following detailed description when considered in connection with the accompanying drawings.

FIG. 1A depicts a working tip (100). FIG. 1B depicts the shaft (40), frustum (20) and apical tip (10). FIG. 1C depicts the apical tip (10), frustum (20) and shoulder portion of the shaft (30).

FIG. 4 provides a close-up of the frustum (20), connector (12), and apical tip (10) of a working end. Reference character (15) describes a distal portion of the arm (15) that holds the fixed, non-rotating apical tip (10) in place. In some embodiments this distal portion of the arm can be removed along with the apical tip from the rest of the arm. Reference character (45) describes a flange on which the arm (15) is mounted. In most embodiments the flange 45 is non-rotatable and anchored to the shaft (40) so as to provide for secure attachment of any removable elements from the shaft, however, in some embodiments the flange (45), frustum roller (20), arm (15) and apical tip (10) may be removed and replaced as a unit.

FIG. 7 depicts one use of the dental instrument on a model of human teeth. As shown, the tapered conical tip of the dental instrument permits improved viewing of working tooth surfaces. Unlike cylindrical rollers, the tapered tip provides an unobstructed view of the working surface. As shown, the frustum roller can easily roll over surfaces of a tooth to evenly distribute a dental restorative material. Unlike rotating or vibrating tips that introduce sheer and result in mixing of an applied dental restorative material with air, the fixed apical tip does not introduce vibrational or rotational sheer.

DETAILED DESCRIPTION OF THE INVENTION

The present disclosure will be better understood with reference to the following definitions:

"Apical tip" refers to portion of the dental instrument distal to the center of the shaft and distal to the frustum roller. Generally, the apical tip will be a most distal portion of the dental instrument. An apical tip may be placed on one or both ends of the dental instrument. In most embodiments the apical tip is fixed to an internal arm and is dimensioned to secure a frustum roller to the dental instrument, for example, it may have a ridge or flange that covers and holds in place the small end of the frustum. In some embodiments, the apical tip can be removed, for example, by rotating it, mechanically unlocking it from the handheld shaft, or by otherwise detaching it from the arm or flange or other member securing it to the shaft of the dental instrument. In other embodiments, the apical tip and frustum roller, or apical tip, frustum roller and arm may be removed and replaced as a unit. Generally, the apical tip will be smooth and/or rounded, however, in some embodiments it may have micro- or nano-texturing to reduce adherence of materials to the tip, provide easier handling of the instrument, or to otherwise facilitate homogenous application of a dental restorative material.

"Shaft", "handheld shaft" or "body" refers to an elongated portion of the dental instrument which is usually configured so that it may be held in a hand. The more distal parts of the shaft from its center point may comprise a tapering waist and a shoulder portion which form portions of, and help position, the working end. The shaft may comprise one or more of metal (e.g., stainless steel, carbon steel which may be coated with an alloy such as nickel-titanium; iron, titanium or aluminum or their durable alloys), plastic, ceramic or composite materials, for example, it may be constructed from a composite resin containing metal, glass, carbon, or resin fibers or fillers. Portions of the shaft may be texturized, fluted, or roughened to provide for a firm grip and dexterous control of the instrument. It may be coated with silicone, plastic, or other coatings to provide a soft and firm grip. This term includes hand-held instruments as well as instruments that may be attached or manipulated by machines, dental equipment, waldos or other devices.

Figure 7:
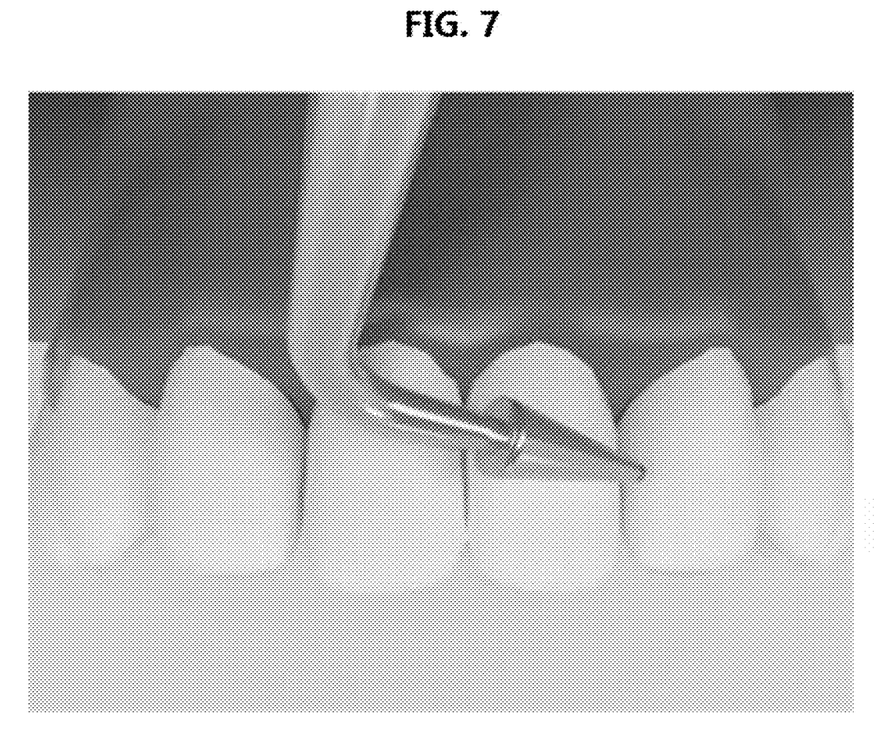

A "frustum" describes a cone that is truncated on both ends. The frustum roller of the invention is positioned between the apical tip and the shaft of the instrument. The frustum is a rotatable component of a "roller tip" which may also include the apical tip, connectors, arms, flanges and other non-shaft elements of the dental instrument. Generally, rotation at the working tip occurs inside the frustum roller around the internal arm but not at the most distal end. In some embodiments the aspect ratio between the base and height of the frustum will range from 1:1, 1:1.5, 1:2, 1:2.5, 1:3, 1:3.5, 1:4, 1:4.5 to 1:5 or any intermediate ratio. An exemplary aspect ratio is shown by FIG. 7. In many embodiments, the roller tip is removable from the working end, such that differently shaped tips may be placed on the working end during the restoration of the tooth, as necessary, to ensure complete and even coverage to an uneven surface. In some embodiments, the frustum may be color-coded, for example, based on its size, aspect ratio between base and length, surface type, rotational ability, or other physical features.

An "arm" (or, alternatively, "pin" or "internal shaft") describes a mechanical element that secures the apical tip to the shaft of the dental instrument. It may further comprise other elements such as one or more bushings, bearings, flanges, washers, collars, gaskets, or connectors that connect the arm to the shaft or help actuate or facilitate rotation of the frustum roller. The arm may be integral with the apical tip, or, in other embodiments, the arm may separate into an internal portion and a removable apical tip. In some embodiments the arm is removable from the shaft to facilitate replacement of the frustum. In other embodiments, such as disposable dental instruments, the apical tip may be permanently bound to the arm, thus locking the frustum roller in place. The arm provides a longitudinal axis around which the frustum rotates and in most embodiments holds the frustum between the apical tip and the shaft in a manner that permits the frustum to rotate around this longitudinal axis.

A "non-stick" material, coating, or film is one to which dental materials, such as tooth restorative materials, do not substantially adhere. The apical tip, frustum and other parts of the dental instrument that come into contact with a dental material may be made of, contain, or be coated with a non-stick material. These materials include polytetrafluoroethylene (PTFE; Teflon®), fluorinated ethylene propylene, perfluoroalkoxy copolymers, carbon fibers and molybdenum disulfide in amounts effective to provide a low coefficient of friction. Anodized aluminum, ceramic, silicone, silane-coated, enameled, lotus-effect, ultrahydrophobic, or self-cleaning materials, coatings or films may also be used. The frustum roller and/or apical tip may comprise a resilient material that has the ability to return to its original shape after a mechanical compression, with no plastic deformation occurring when subjected to mechanical stress in normal dental procedures. The frustum roller and apical tip may advantageously comprise materials having low surface energy, for example, less than 30, 25, 20, 15, or 10 mN/m, which contribute to low adhesion with the restorative composite materials. Examples of such resilient materials include silicones, polyurethanes, and thermoplastic elastomers. The frustum roller and/or apical tip may comprise a fluorine-charged thermoplastic vulcanizate, such as the Viton™ fluoroelastomers from DuPont Dow Elastomers, Wilmington, Del. and Fluoroprene™ from Freudenberg-NOK, Plymouth, Mich., which each contain 40-70 wt. % fluorine. These fluorine charged materials have low surface tension, on the order of 18-20 mN/m, and thus, have low adhesion to the restorative composite materials. In an exemplary embodiment, the roller tip material has a Shore A hardness of 20-60, and preferably, the roller tip has a Shore A hardness on the order of 30. The roller tip material may be a solid material or a microporous material. The frustum rollers and/or apical tips may have different shapes, hardnesses, textures and colors, for example, the physical form or properties of a replaceable frustum roller or apical tip may be color coded. Any of the surfaces of the dental instrument of the invention may be coated or partially coated with a non-stick material to reduce adherence of restorative material or friction between parts, especially, the apical tip, frustum, or other surface coming into contact with restorative dental materials. Preferably the apical tip and the frustum are made of different materials having a difference in surface properties such as water contact angle. The water contact of the apical tip is preferably less than 90° whereas the water contact of the frustum is preferably more than 90°. Preferably there is a difference of at least 10°, more preferably at least 15°, 20°, 25°, 30°, 40°, 45° or 50° between the water contact angles for the apical tip and the frustum.

"Restorative dental materials" or "dental composite resins" include synthetic resins which are used in dentistry as restorative material or adhesives. Synthetic resins evolved as restorative materials since they are insoluble, aesthetic, insensitive to dehydration, easy to manipulate and reasonably inexpensive. Composite resins are most commonly composed of Bis-GMA and other dimethacrylate monomers (TEGMA, UDMA, HDDMA), a filler material such as silica and in most current applications, a photoinitiator. Dimethylglyoxime is also commonly added to achieve certain physical properties such as flow ability. Glass ionomer cements are also contemplated. Further tailoring of physical properties of these materials may be achieved by formulating unique concentrations of each constituent.

Taking into consideration the problems described above for conventional dental instruments, including obscured views of working surfaces, incorporation of bubbles into a restoration, and nonhomogeneous application of dental materials, the inventors developed the dental instruments described herein.

The inventors provide herein a strong and durable dental instrument, designed to facilitate easy and accurate placement of a dental restorative material and to have low stick properties that resist adherence of dental restoration resins.

The size of the instrument and its working end is selected so that it can distribute the restorative material on a tooth surface, including into or onto a cavity surface. Most embodiments of the dental instrument of the invention are sized proportionately to human teeth. However, the size of an instrument and its working end may vary depending on the dimensions of the surface or teeth being restored. For example, it may be configured to conform to different arch forms of teeth, such as sized to convenient treat teeth in a squared, tapered or ovoid arc, it may be sized based on the age of the patient, or sized proportionate to any non-human teeth or dental surfaces being treated. The skilled practitioner will be able to size the dental instrument appropriately for use professional practice. FIG. 7 provides an example of a dental instrument. Generally, the dental instrument will be about the same size as that shown in FIG. 7 or within a size range of 0.5 to 1.5-times the size depicted in FIG. 7. This range includes all subranges and intermediate values such as 0.5, 0.6, 0.7, 0.8, 0.9, <1.0, 1.0, >1.0, 1.1, 1.2, 1.3, 1.4, <1.5 and 1.5. In some embodiments, the length of the shaft ranges from about 8 to 14 cm and its diameter ranges from about 1 to 3 mm; the length of the roller ranges from about 4 to 10 mm and the diameter of the roller ranges from 2 to 6 mm at its base to about 0.5 to 2 mm at its tip; the apical tip ranges in length and width from about 0.5 to 2 mm.

In most embodiments, the dental instrument is durable, hard, resistant to damage during and between uses and is made from materials that present little or no risk of discoloring dental restorative materials. In many embodiments it is durable and long-lived capable of reuse. It may be produced from lightweight materials and with a handle or handheld body that improves the tactile sensitivity of a practitioner during use thus allowing easy and accurate placement, manipulation and sculpting of dental restorative materials. It can exhibit a lower coefficient of friction and a higher contact angle with a dental restorative material than many conventional dental instruments.

The dental instrument of the invention will conform to safe dental practices. It is made of materials recognized as safe for dental instruments and can be sterilized to avoid introduction of contaminants or cross-contaminants into the mouth of a patient. In some embodiments the instrument is reusable and will be made materials that can be autoclaved, irradiated, or chemically sterilized between uses. In other embodiments, the instrument will be provided as a sterile and disposable product so as to avoid the risk of producing cross-contamination between patients entirely.

The dental instrument of the invention comprises a working tip comprising a non-moving apical tip and a frustum roller. In contrast to dental instruments with cylindrical or other shaped tips, the substantially conical working tip of the invention provides an unobstructed view of the operating area or working surface. In comparison, a cylindrical roller body will obstruct the view. The frustum roller tip of the invention permits better control of application and spreading of dental restorative material in proximal areas of teeth. Moreover, the frustum roller and apical tip presents a smaller working area compared to a cylindrical working tip thus providing better control of application or packing of a dental restoration as well as reducing or eliminating incorporation of bubbles into a restoration.

The rotating frustum of the dental instrument of the invention permits easy distribution of the restorative material on the tooth surface and prevents sticking or adhesion of restorative material to the instrument.

The design of the dental instrument of the invention reduces the amount of time for a practitioner to apply and aesthetical spread, sculpt, and feather a dental restorative material without introducing bubbles. Exposure of the mouth to natural light reduces the working time for applying an unpolymerized dental restorative material that is polymerized with light. The incorporation of bubbles into a polymerizing dental restorative material decreases the strength of a dental restoration. Increasing speed of application is important to provide time for uniform and bubble-free application of the dental restorative material prior to substantial polymerization of the material. This time savings is attributable to use of a fixed rounded apical tip and rotating frustum which provide for speedy, uniform and bubble-free application of dental materials.

The invention substantially eliminates unwanted adhesion of dental restorative material to the dental instrument and facilitates placement, manipulation, sculpting and feathering of a dental restorative material. It permits non-impressive micro-manipulation of a restorative resin, reduces resin pullback, and leaves no discernable footprint in uncured restorative after use and withdrawal of the dental instrument. This permits seamless ultra-thin feathering of a resin desirable for strength, smoothness, durability and aesthetic properties of a dental restoration. Moreover, when a procedure uses a protective sheaf or emulsion, the instrument may be used to microdisplace a dental restorative material through these materials.

In most embodiments, the dental instrument of the invention will have an elongated shaft with a handle portion and one or two working ends extending therefrom. A roller tip comprising a fixed apical tip and a frustum roller may be mounted on the shaft by rotating it on the working end so as to rotate about a center axis of the end of the instrument.

Features of the invention are now described with reference to FIGS. 1 to 7. These figures describe, using common reference characters, components and other features of the dental instrument of the invention.

Figure 1A:
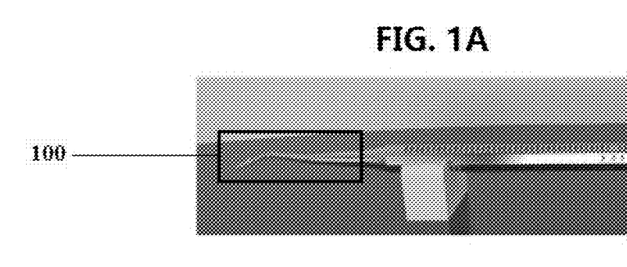
FIGS. 1A, 1B and 1C depict a dental instrument having one or two working tips (FIGS. 1A and 1B) and a working tip with a metal shoulder portion, frustum roller, and an apical tip that is attached to an internal arm.
Figure 1B:
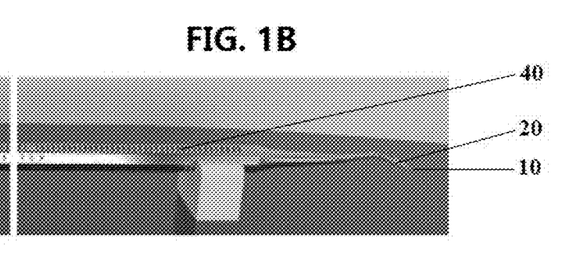
Figure 1C:
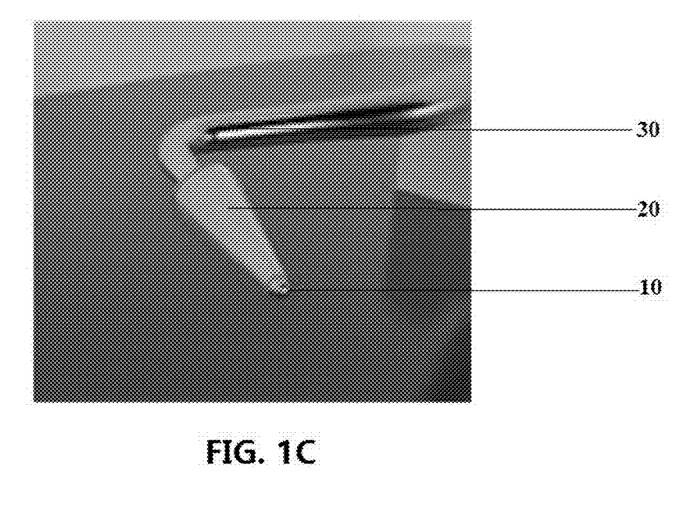

FIGS. 1A and 1B together depict a dental instrument with a working end (100) at both ends of the shaft (40). The working end comprises a frustum roller (20) and a fixed apical tip (10). FIG. 1C provides a closer view of the working end which comprises a shoulder (30), frustum roller (20) and apical tip (10). A working end or portions thereof may be removable from the shaft and replaceable. This fixed apical tip (10) of the invention avoids introduction of bubbles into a dental restorative compared to rotating or vibrating tips of some conventional dental instruments which act as mixers and introduce bubbles into a restorative.

As shown by FIG. 10, this dental instrument is advantageously designed to aesthetically distribute tooth restorative materials on a tooth surface within the oral cavity of a patient while avoiding problems associated with adherence of restorative materials to prior art instruments, such as inhomogeneous distribution and bubble formation. The dental instrument of the invention may also be used to distribute dental restorative materials on natural teeth or on artificial tooth surfaces or teeth.

Figure 2A:
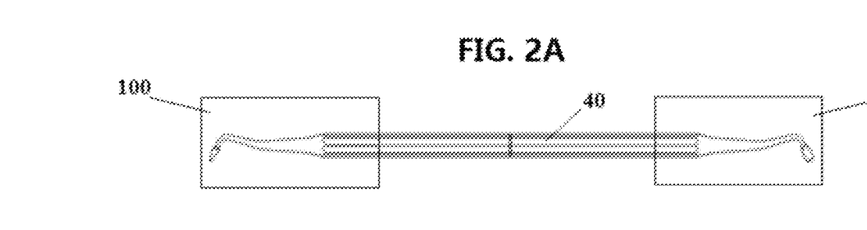
FIGS. 2A and 2B provide two views of an instrument with a central shaft (40) by which the instrument may be held in the hand or by the fingers and two working ends (100) each in the same plane.
Figure 2B:
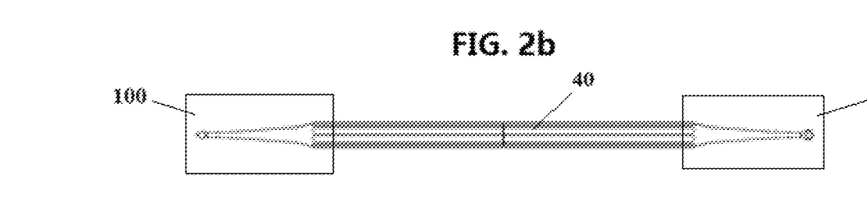

FIGS. 2A and 2B provide a top and side view of the dental instrument. The central shaft may be fluted or otherwise textured to provide a firm grip and a high degree of manual control over the instrument. As shown the instrument has two working ends (100) extending from opposite ends of the shaft. As shown in FIG. 2A, each working end (100) has a different tip. In many embodiments each working end will be the same but may be oriented differently with respect to the shaft (40).

In FIG. 2A, each tip angled away from the longitudinal axis of the shaft within a range of 0 to 90 degrees. In some embodiments, one tip will point down and the other up with respect to the other tip. As shown by the top view in FIG. 2B, each tip may be in the same plane. In other embodiments one tip may be rotated out of the plane with respect to the other tip, for example, one tip may be rotated by 45 degrees in one direction and the other 45 degrees in the other direction. Depending on the tooth or other surface to be restored, differently angled working ends allow the practitioner to choose the appropriate angle for most effectively distributing the restorative material on the tooth surface, particularly where the tooth surface is located in the oral cavity.

Figure 3:
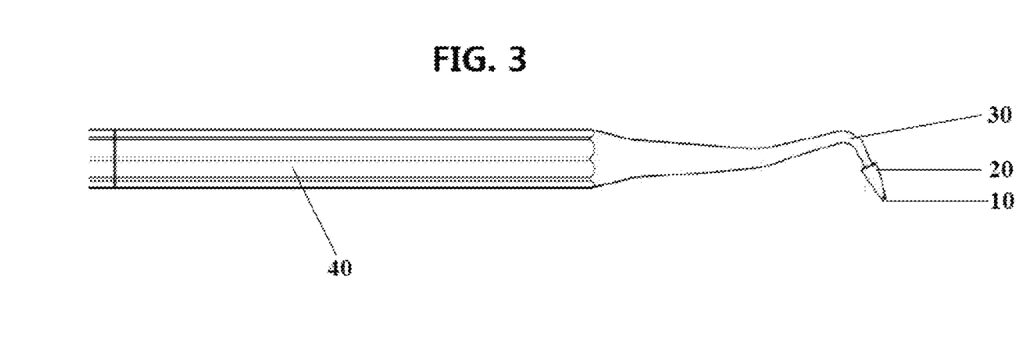
FIG. 3 shows a central shaft (40) attached via a tapered shoulder (30) to a conical tip comprising a rotating frustum (20) and a fixed apical tip (10). The frustum (20) and apical tip (10) may be angled by adjusting the orientation of the shoulder (30).

FIG. 3 depicts the working end in relationship to the center of the shaft. As shown the distal portion of the working end comprising the distal part of the shoulder (30), the frustum (20) and the apical tip (10) is pointed downward at approximate 45 degrees in relation to the longitudinal axis of the shaft (40). In other embodiments the orientation of the tip may vary between 0 degrees (co-axial with the axis of the shaft) and 90 degrees (perpendicular to the axis of the shaft). The particular angles for the first and second working ends (100) depicted in FIG. 3 are not intended to limit the configuration of the working ends of other embodiments of the invention.

Figure 4:
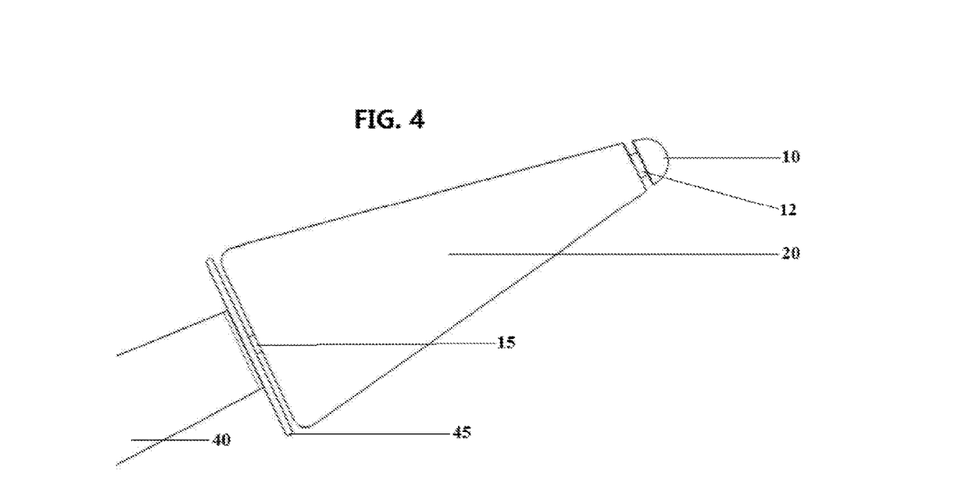
Figure 5:
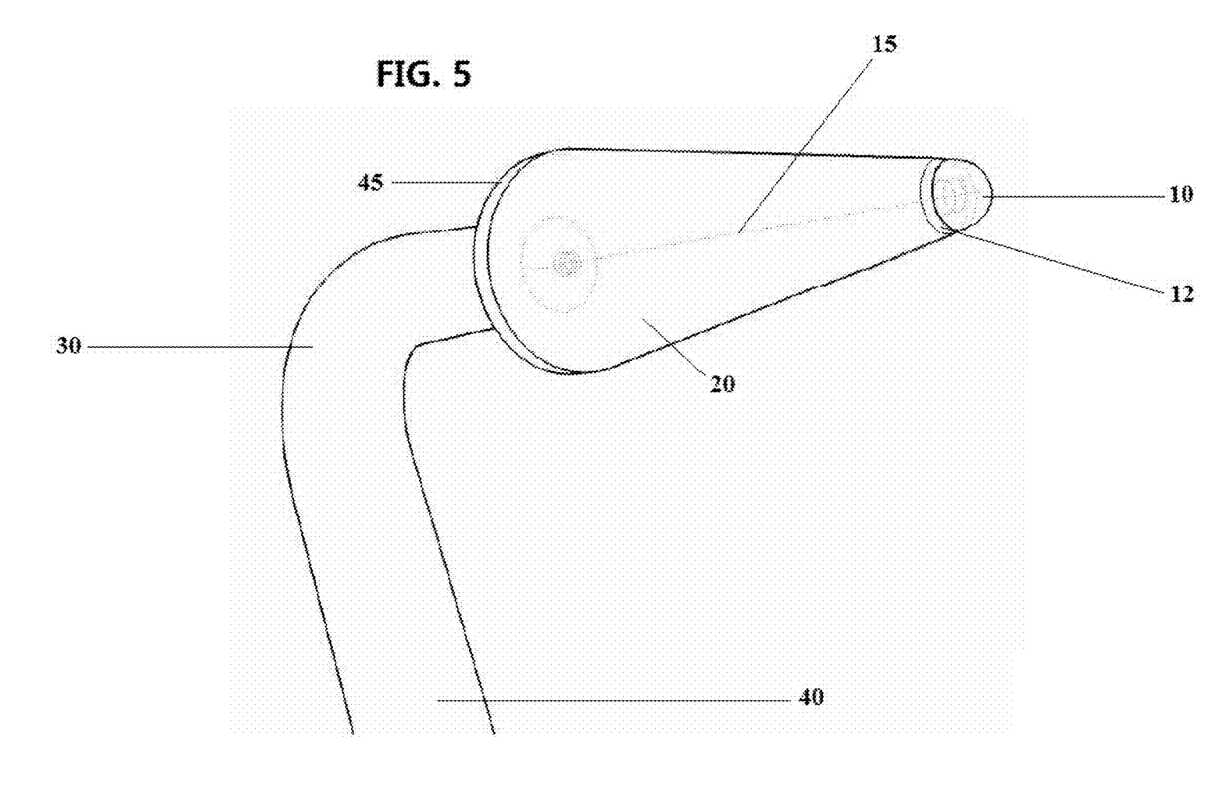
FIG. 5 provides a view of the frustum (20), connector (12), and a fixed rounded apical tip (10) of the working end. Reference character (45) describes a flange on, or through which the distal portion of the arm (15) is mounted. A shoulder portion of the shaft is identified by (30) and the shaft by (40).
Figure 6:
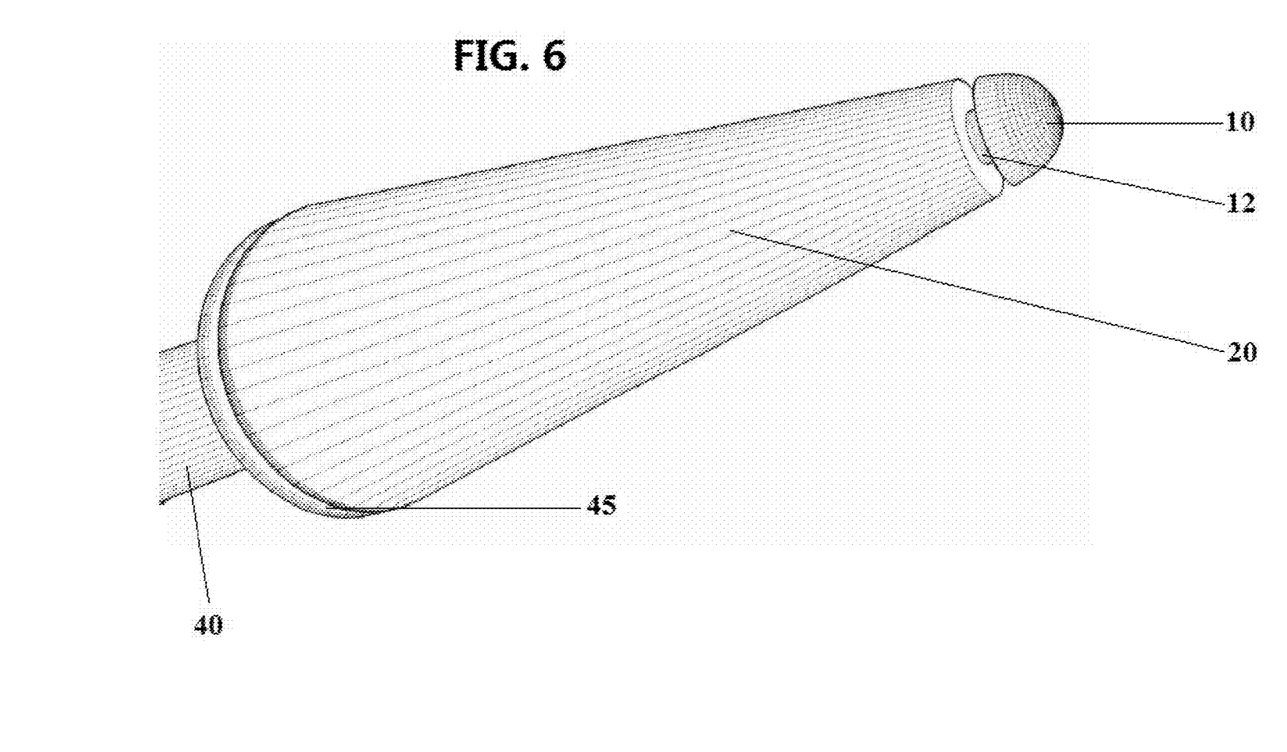
FIG. 6 provides a view of the apical tip (10), connector (12), frustum (20), a flange (45) and the shaft (40). The arm (15) goes through the center of connector (12) an attaches to the apical tip (10). The connector (12) may be made of a low friction material and reduce friction between the frustum roller (20) and the fixed apical tip (10). In most embodiments, the connector (12) and the arm (15) are integral. However, in others they may be independently present. In some embodiments the connector (12) and arm (15) may be, independently, present.

FIGS. 4, 5 and 6 show the working tip of the dental instrument including a rounded apical tip (10), a distal portion of the arm (15), the frustum roller (20), a flange or connector (45) between a distal portion of the shaft into or onto which the arm (15) is inserted or mounted. In some embodiments a ring-shaped washer, spacer or other element (12) is arranged between the apical tip and the frustum roller (20). This element (12) may be made of a low friction material to reduce friction and wear between the fixed apical tip and the frustum roller (20). The distal portion of the arm next to the rounded tip may be thicker or thinner and detachable from the more proximal part of the arm (20). It may be unlockable or otherwise removable along with the fixed apical tip to permit removal and replacement of the frustum (20). In another embodiment, the proximal and distal portions of the arm are integral but detachable from the apical tip (10) and/or detachable from the shaft, permitting removal and replacement of the frustum (20) and/or arm (15) or apical tip (10). A flange (45) may be arranged below or as part of the base of the frustum (20). This may be firmly connected to the shaft (40) and not rotatable, it may be attached to the base of the frustum roller (20), or it may be independent of both the frustum roller and shaft and serve as a lubricating or low friction member to reduce friction and wear between the base of the frustum roller (20) and the shaft (40). When integral with the base of the frustum (20), it may be ring-shaped to provide a space through which the arm may go to connect it with the shaft (40). When integral with the shaft (40), it may comprise an anchor or connector for the proximal end of arm (20).

EMBODIMENTS

The following embodiments illustrate various aspects of the present invention. They are not to be construed to limit the claims in any manner whatsoever. The invention is directed to dental instruments as well as methods of using these dental instruments to provide dental restorations with superior durability, strength, and aesthetics that are substantially free of bubbles.

In one embodiment the invention is directed to dental instrument suitable for distributing a restorative material on a surface of a tooth that comprises a handheld shaft having one or two working ends, said working end(s) comprising a shoulder with an distally projecting arm around which is longitudinally mounted a frustum roller that has its narrow section projecting away from the center of the shaft and that is capped by an end of the arm; wherein the frustum conical body is mounted on the arm so that it can rotate around its longitudinal axis; and wherein the working ends are sized to distribute a restorative material on a surface of a tooth. In most embodiments the internal arm is fixed, does not rotate, and locks or mounts the rotatable frustum to the shaft along a longitudinal axis defined by the arm. In some embodiments the arm may be designed to rotate along with the frustum but be attached to the non-rotating apical tip in a manner that does not rotate the tip, e.g., it may have a fixed inner arm attached to the shaft that is surrounded by a concentric cylinder that rotates with the frustum. The frustum body and optionally the arm and apical tip may be removable and replaceable.

In another embodiment, the dental instrument includes two working ends extending in opposing directions from the handle portion to provide different angles for the working ends or to provide differently size roller tips on the working ends.

In some embodiments, a center axis of the shaft and the center axis of at least one working end are coaxial with apical tip being oriented at 0 degrees with respect to the shaft axis. In other embodiments, the shaft axis and the axis of the working end ending in an apical tip angled >0-90 degrees with respect to the center axis of the handheld shaft. This range includes all intermediate values and subranges such as 0, 10, 15, 20, 25, 30, 45, 50, 55, 60, 65, 70, 75, 80, 85, <90, and 90 degrees.

Some embodiments of the dental instrument further comprise one or more bushings or bearings rotatably mounted on the working end proximal to the shaft so that the frustum is rotated on the working end by means of the at least one bushing or bearing.

In some embodiments the dental instrument has two working ends each of which, independently, is angled 0-90 degrees with respect to the center axis of the shaft. This range includes all intermediate values and subranges such as 0, 10, 15, 20, 25, 30, 45, 50, 55, 60, 65, 70, 75, 80, 85, <90, and 90 degrees. These working ends may have the same kinds of tips, e.g., an assembly of the same frustum and apical tip, or may contain different working tips. For example, one working tip may contain a frustum roller according to the invention and the other working tip flat spatulate tip, a cylindrical tip, scaling tip, or other conventional fixed or movable dental tips used to make or repair dental restorations. This provides a convenient dual use tool and reduces the time needed to complete the restoration work.

Some embodiments of the dental instrument will feature to two working ends each of which, independently, is angled 0-90 degrees with respect to the center axis of the shaft. For example the apex of a working end may be coaxial at 0 degrees with respect to, or perpendicular at 90 degrees with respect to, the longitudinal axis of the shaft. This range includes all intermediate values and subranges such as 0, 10, 15, 20, 25, 30, 45, 50, 55, 60, 65, 70, 75, 80, 85, <90, and 90 degrees.

Other embodiments of the dental instrument will have two working ends each of which, independently, is angled 0-90 degrees with respect to the center axis of the shaft; and further where each working end is radially angled 0-180 degrees with respect to the other working end. For example, one working end may be perpendicular with respect to the longitudinal axis of the shaft and face in the opposite direction to the other working end (i.e., be at relative angle of 180 degrees with respect to the other working end). This range includes all intermediate values and subranges such as 0, 10, 15, 20, 25, 30, 45, 50, 55, 60, 65, 70, 75, 80, 85, <90, 90, 100, 105, 110, 115, 120, 125, 130, 140, 145, 150, 155, 160, 165, 170, 175, <180, and 180 degrees. This permits a practitioner to select a tip angled or positioned to most conveniently and effectively treat a dental surface.

In some embodiments, the shaft, shoulder, waist, arm, frustum, apical tip, or other structural elements disclosed herein comprise metal, such as carbon steel or stainless steel. In other embodiments one or more of these components may be made of, contain, or be coated with a silicone, thermoplastic elastomer or polyurethane.

Materials used to construct the dental instrument may contain additional structural or compositional elements such as metal, glass, polymer, or carbon fibers or fillers. For example, the shaft, pin and/or frustum may be composed of a durable plastic which contains glass fibers or carbon fibers. In other embodiments, the device will substantially be composed of metal which may be coated with another material such as a plastic resin or silicone to improve the handleability or non-adherent properties of the instrument. For example, a handle portion of the shaft may be coated with plastic to provide a firm grip or a frustum or apical tip may be coated with a durable non-stick material. Alternatively, the shaft may be textured or fluted to provide a firm grip.

In some embodiments, the working end of the dental instrument of the invention will comprise a material that contains or is coated with a non-stick material or coating, such as polytetrfluoroethylene ("PTFE"), a silicone, a thermoplastic elastomer, or polyurethane. The working end may comprise at least one material having a Shore A hardness (ASTM D2240 00) ranging from approximately 20-80. This range includes all intermediate values and subranges, such as 20, 21, 25, 30, 35, 40, 45, 50, 60, 70, 75, 79, <80 and 80.

Another embodiment of the invention pertains to a method for distributing a restorative material on a surface of a tooth comprising applying the restorative material to a surface of a tooth or dental prosthetic and distributing it with a tool of other embodiments. In some embodiments of this method a dental material is applied or packed into a cavity in a tooth or into or over a depression or imperfection in a prior dental restoration or prosthetic.

Terminology used herein is for the purpose of describing particular embodiments only and is not intended to be limiting of the invention.

The headings (such as "Background" and "Summary") and sub-headings used herein are intended only for general organization of topics within the present invention, and are not intended to limit the disclosure of the present invention or any aspect thereof. In particular, subject matter disclosed in the "Background" may include novel technology and may not constitute a recitation of prior art. Subject matter disclosed in the "Summary" is not an exhaustive or complete disclosure of the entire scope of the technology or any embodiments thereof. Classification or discussion of a material within a section of this specification as having a particular utility is made for convenience, and no inference should be drawn that the material must necessarily or solely function in accordance with its classification herein when it is used in any given composition.

As used herein, the singular forms "a", "an" and "the" are intended to include the plural forms as well, unless the context clearly indicates otherwise.

It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof.

As used herein, the term "and/or" includes any and all combinations of one or more of the associated listed items and may be abbreviated as "/".

Links are disabled by insertion of a space or underlined space into a link, for example, before "www" or after "//" and may be reactivated by removal of the space.

As used herein in the specification and claims, including as used in the examples and unless otherwise expressly specified, all numbers may be read as if prefaced by the word "substantially", "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), +/−15% of the stated value (or range of values), +/−20% of the stated value (or range of values), etc. Any numerical range recited herein is intended to include all sub-ranges subsumed therein.

Disclosure of values and ranges of values for specific parameters (such as temperatures, molecular weights, weight percentages, etc.) are not exclusive of other values and ranges of values useful herein. It is envisioned that two or more specific exemplified values for a given parameter may define endpoints for a range of values that may be claimed for the parameter. For example, if Parameter X is exemplified herein to have value A and also exemplified to have value Z, it is envisioned that parameter X may have a range of values from about A to about Z. Similarly, it is envisioned that disclosure of two or more ranges of values for a parameter (whether such ranges are nested, overlapping or distinct) subsume all possible combination of ranges for the value that might be claimed using endpoints of the disclosed ranges. For example, if parameter X is exemplified herein to have values in the range of 1-10 it is also envisioned that Parameter X may have other ranges of values including 1-9, 2-9, 3-8, 1-8, 1-3, 1-2, 2-10, 2.5-7.8, 2-8, 2-3, 3-10, and 3-9, as mere examples.

As used herein, the words "preferred" and "preferably" refer to embodiments of the technology that afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the technology.

As referred to herein, all compositional percentages are by weight of the total composition, unless otherwise specified. As used herein, the word "include," and its variants, is intended to be non-limiting, such that recitation of items in a list is not to the exclusion of other like items that may also be useful in the materials, compositions, devices, and methods of this technology. Similarly, the terms "can" and "may" and their variants are intended to be non-limiting, such that recitation that an embodiment can or may comprise certain elements or features does not exclude other embodiments of the present invention that do not contain those elements or features.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Spatially relative terms, such as "under", "below", "lower", "over", "upper", "in front of" or "behind" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

The description and specific examples, while indicating embodiments of the technology, are intended for purposes of illustration only and are not intended to limit the scope of the technology. Moreover, recitation of multiple embodiments having stated features is not intended to exclude other embodiments having additional features, or other embodiments incorporating different combinations of the stated features. Specific examples are provided for illustrative purposes of how to make and use the compositions and methods of this technology and, unless explicitly stated otherwise, are not intended to be a representation that given embodiments of this technology have, or have not, been made or tested.

REFERENCES

Further background information and descriptive support for dental restoration materials and useful features of dental instruments may be found in one or more of the following references which are incorporated by reference.

Gray, H. S., Gavin, J. B. The surface texture of trimmed composite fillings. A scanning electron microscopy study. NZ Dent J. 1975; 71:139-145.

Hietanen, J., Rantanen, A. V. Evaluation of different composite finishing methods. Proc Finn Dent Soc. 1976; 72:11-18.

Lutz, F. Beitrage zur Entwicklung von Seitenzahn-Komposits. KAR PAR PZM Verlag, Zurich; 1980:1/7-75/7.

McCabe, J. F., Caddick, R. J. The finishing of composite restorations. Br Dent J. 1978; 145:101-104.

Valcke, C. F. Some surface characteristics of composite resin filling materials. J Dent Assoc S Afr. 1978; 33:21-27

Porte, A. Cavity design for composite resin. (Others) AADR Program and Abstracts, 1983 (Abstract no. 764).

Oilo, G., Jorgensen, K. D. Effect of beveling on the occurrence of fractures in the enamel surrounding composite resin fillings. J Oral Rehabil. 1977; 4:305-309.

Dennison, J. B., Craig, R. G. Physical properties and finished surface texture of composite restorative resins. JADA. 1972; 85:101-108.

Finger, W., Jorgensen, K. D. Polymerisationsinhibition durch Sauerstoffbei Kompositfullungsmaterialien und Schmelzversieglern. Schweiz Mschr Zahnheilk. 1976; 86:812-824.

Hannah, C. Mcd. Smith, G. A. The surface finish of composite restorative materials. Br Dent J. 1973; 135:483-488.

Heath, J. R., Wilson, H. J. Surface roughness of restorations. Br Dent J. 1976; 140:131-137.

McLundie, A. C., Murray, F. D. Comparison of methods used in finishing of composite resin—a scanning electron microscopy study. J Prosthet Dent. 1974; 31:163-171.

De Gee, A. J., Ten Harkel, H. C. Abrasion of composite materials by toothbrushing. J Dent Res. 1982; 61:571 (abstract no. 61).

Bartenstein, U., Finger, W. Bestimmung der Oberflachengute von Composite-Fullungsmaterialien. Dtsch Zahnaerztl Z. 1974; 29:276-282.

Forsten, L. Fracturing of marginal enamel when finishing composite fillings with rotary instruments. Proc Finn Dent Soc. 1977; 73:38-39.

Tolley, L. G., Dennison, J. B., O'Brien, W. J. Surface finish of composite materials. J Dent Res. 1977; 56:217 (abstract no. 663).

Chandler, H. H., Bowen, R. L., Paffenbarger, G. C. Method for finishing composite restorative materials. JADA. 1971; 83:344-348.

Lutz, F., and Phillips, R. W. Classification of composite resin systems and their evaluation. J Prosthet Dent, to be published.

Lambrechts, P., Vanherle, G. Observation and comparison of polished composite surfaces with the aid of SEM and profilometer. J Oral Rehabil. 1982; 9:169-182.

Nathanson, D., Dogon, I. L., Van Leeuwen, M. J. A comparison of a new method for finishing composite restorations with conventional techniques—in vivo study. J Dent Res. 1978; 57:367 (abstract no. 1170).

Ferreira, M. R., De Wet, F. A. Effect of finishing agents on new restorative resins: a SEM study. J Dent Res. 1982; 61:605 (abstract no. 22).

Louka, A. N., Stillwater, J. C. Effectiveness of different finishing systems on composite resin surfaces. J Dent Res. 1982; 61:302 (abstract no. 1113).

Johnson, L. N., Jordan, R. E., Lynn, J. A. Effects of various finishing devices on resin surfaces. JADA. 1971; 83:321-331.

Volchansky, A., Cleaton-Jones, P. Study of surface characteristics of natural teeth and restorations adjacent to gingivae. J Prosthet Dent. 1974; 31:411-421.

Sokal, R. R., Rohlf, F. J. Biometry. W. H. Freeman, San Francisco; 1981:248.

Lutz F, Setcos J, Phillips R. New finishing instruments for composite resins. J Am Dent Assoc. 1983; 107:575-580.

Fruits T, Miranda F, Coury T. Effect of equivalent abrasive grit sizes utilizing differing polishing motion on selected restorative materials. Quintessence Int. 1996; 27:279-285.

Oward S. Glazer, DDS, FAGD. Can an Instrument Make a Difference?

Ivoclar Vivadent. Optra sculpt Pad: Modeling instrument for composite filling materials. Amherst, N.Y.: Ivoclar Vivadent: 2005:1-2.

All publications and patent applications mentioned in this specification are herein incorporated by reference in their entirety to the same extent as if each individual publication or patent application was specifically and individually indicated to be incorporated by reference, especially referenced is disclosure appearing in the same sentence, paragraph, page or section of the specification in which the incorporation by reference appears.

The citation of references herein does not constitute an admission that those references are prior art or have any relevance to the patentability of the technology disclosed herein. Any discussion of the content of references cited is intended merely to provide a general summary of assertions made by the authors of the references, and does not constitute an admission as to the accuracy of the content of such references.

The invention claimed is:

1. A dental instrument, comprising
a shaft and at least one a working end, said working end comprising an arm attached to, and projecting away from the shaft around which arm is a longitudinally mounted conical frustum roller that has a narrow section projecting away from the shaft and that is capped by a non-rotating rounded apical tip which forms an integral or detachable part of the arm; and wherein the frustum roller is mounted on the arm so that it can rotate around the longitudinal axis of the arm,
wherein the arm is mounted on a non-rotatable flange, is fixed and does not rotate, and the non-rotatable flange having a diameter greater than a distal end of the shaft.

2. The dental instrument of claim 1, wherein the frustum roller consists of a conical frustum that can rotate.

3. The dental instrument of claim 1, wherein the frustum roller is removable and replaceable.

4. The dental instrument of claim 1, wherein the arm, a body of the frustum roller, and apical tip are removable and replaceable.

5. The dental instrument of claim 1 that has one working end on one end of the shaft.

6. The dental instrument of claim 1 that has two working ends one each end of the shaft.

7. The dental instrument of claim 1, wherein the shaft has a center axis and the center axis of at least one working end is angled 0-90 degrees with respect to the center axis of the shaft.

8. The dental instrument of claim 1, wherein the shaft has a center axis and the center axis of at least one working end is angled 40-50 degrees with respect to the center axis of the shaft.

9. The dental instrument of claim 1, further comprising one or more bushings or bearings rotatable mounted on the working end operatively connected to the frustum.

10. The dental instrument of claim 1 that has two working ends each of which, independently, is angled 0-90 degrees with respect to the center axis of the shaft.

11. The dental instrument of claim 1 that has two working ends each of which, independently, is angled 40-50 degrees with respect to the center axis of the shaft.

12. The dental instrument of claim 1 that has two working ends each of which, independently, is angled 0-90 degrees with respect to the center axis of the shaft; and wherein each working end is radially angled 0-180 degrees with respect to the other working end.

13. The dental instrument of claim 1, wherein the shaft, arm, frustum, and/or apical tip comprise metal.

14. The dental instrument of claim 1, wherein the shaft, arm, frustum, and/or apical tip comprise a plastic which optionally contains metal, glass, ceramic, carbon or polymer fibers.

15. The dental instrument of claim 1, wherein the shaft, arm, frustum, and/or apical tip is made of, contains, or is coated with a non-stick material.

16. The dental instrument of claim 1, wherein the shaft, arm, frustum, and/or apical tip is made of, contains, or is coated with polytetrgfluoroethylene ("PTFE").

17. The dental instrument of claim 1, wherein the shaft, arm, frustum, and/or apical tip is made of, contains, or is coated with at least one of a silicone, a thermoplastic elastomer, or a polyurethane.

18. The dental instrument of claim 1 wherein the shaft, arm, frustum, and/or apical tip is made of, contains, or is coated with at least one material having a Shore A hardness (ASTM D2240 00) ranging from approximately 20-80.

19. A method for distributing a restorative material on a surface of a tooth comprising applying the restorative material to a surface of a tooth or dental prosthetic, or cavity, and distributing it with the dental instrument of claim 1.

* * * * *